US010548956B2

(12) United States Patent
Har-Noy

(10) Patent No.: US 10,548,956 B2
(45) Date of Patent: *Feb. 4, 2020

(54) ALLOGENEIC CELLULAR IMMUNOTHERAPY FOR OPPORTUNISTIC INFECTION

(71) Applicant: Immunovative Therapies, Ltd., Jerusalem (IL)

(72) Inventor: Michael Har-Noy, Jerusalem (IL)

(73) Assignee: MIRROR BIOLOGICS, INC., Jerusalem (IL)

( * ) Notice: Subject to any disclaimer, the term of this patent is extended or adjusted under 35 U.S.C. 154(b) by 0 days.

This patent is subject to a terminal disclaimer.

(21) Appl. No.: 14/500,395

(22) Filed: Sep. 29, 2014

(65) Prior Publication Data
US 2015/0024006 A1 Jan. 22, 2015

Related U.S. Application Data

(63) Continuation of application No. 11/251,585, filed on Oct. 14, 2005, now Pat. No. 8,865,224.

(60) Provisional application No. 60/618,682, filed on Oct. 14, 2004.

(51) Int. Cl.
A61K 39/00 (2006.01)
(52) U.S. Cl.
CPC ...... *A61K 39/0002* (2013.01); *A61K 39/0005* (2013.01); *A61K 2039/5158* (2013.01); *A61K 2039/57* (2013.01)
(58) Field of Classification Search
None
See application file for complete search history.

(56) References Cited

U.S. PATENT DOCUMENTS

| 6,156,312 A | 12/2000 | Leskovar et al. |
| 6,451,316 B1 | 9/2002 | Srivastava |
| 8,273,377 B2 | 9/2012 | Har-Noy |
| 2003/0175272 A1 | 9/2003 | Gruenberg |

FOREIGN PATENT DOCUMENTS

WO  WO 2005/002504  * 1/2005

OTHER PUBLICATIONS

Romani et al. Current Opinion in Immunology, vol. 9, issue 4, pp. 484-490, 1997.*
Kaufman RM, Anderson KC. Transfusion-Associated Graft-Versus-Host Disease. In: Kufe DW, Pollock RE, Weichselbaum RR, et al., editors. Holland-Frei Cancer Medicine. 6th edition. Hamilton (ON): BC Decker; 2003. Available from: https://www.ncbi.nlm.nih.gov/books/NBK12934/.*
Hempel et al. Bone Marrow Transplantation (1997) 20, 365-368.*
Howland et al. J. Immunol, 2000; 164:4465-4470.*
Riddell et al. Science. vol. 275(5067):238-241. Jul. 1992.*
Office Action, Japanese Patent Application No. 2009505345 Allogeneic Cell Therapy for Treatment of Opportunistic Infection, Jan. 31, 2012.
Perruccio, Katia et al., Transferring functional immune responses to pathogens after haploidentical hematopoietic transplantation, Blood Journal, Dec. 15, 2005, vol. 106, No. 13, pp. 4397-4406.
Beck, Olaf et al., Generation of highly purified and functionally active human Th1 cells against Aspergillus fumigatus, Blood Journal, Mar. 15, 2006, vol. 107, No. 6, pp. 2562-2569.
Einsele, H., Antigen-specific T cells for the treatment of infections after transplantation, The European Hematology Journal, 2003, vol. 4, pp. 10-17.
Bellocchio, S. et al., Immunity to Aspergillus fumigatus: the basis for immunotherapy and faccination, Medical Mycology Supplement, 2005, vol. 43, pp. S181-S188.
European Search Report, dated Jun. 5, 2009.
Lou et al. Cancer Research. Sep. 15, 2004; 64 (18):6783-6790.
National Cancer Institute Factsheet: Bone Marrow Transplantation and Peripheral Blood Stem Cell Transplantation. Oct. 29, 2008. (http://www.cancer.gov/cancertopics/factsheet/therapy/bone-marrow-transplant).
Mencacci et al. Blood Mar. 2001 vol. 97:1483-1490.
Kelsall et al. Annals New York Academy of Sciences vol. 795, pp. 116-126.
Waller et al. Blood, Nov. 1999, vol. 94, pp. 3222-3233.
Bozza et al. Blood, Nov. 2003, vol. 102, 10; published online Jun. 5, 2003.
Kawakami, K. (2003). "Promising Immunotherapies with Th1-Related Cytokines Against Infectious Diseases." Journal of Infection and Chemotherapy, vol. 9, No. 3, pp. 201-209.
Kidd, P. (2003). "Th1/Th2 Balance: The Hypothesis, its Limitations, and Implications for Health and Disease." Alternative Medicine Review, vol. 8, No. 3, pp. 223-246.
Antin, J. H. and J. L. Ferrara (1992). "Cytokine dysregulation and acute graft-versus-host disease." Blood, vol. 80, No. 12, pp. 2964-2968.
Banchereau, J. et al. (1998). "Dendritic cells and the control of immunity." Nature, vol. 392, No. 6673, pp. 245-252.
Bauman, S. K. et al. (2003). "Effects of tumor necrosis factor alpha on dendritic cell accumulation in lymph nodes draining the immunization site and the impact on the anticryptococcal cell-mediated immune response." Infection and Immunity, vol. 71, No. 1, pp. 68-74.
Bennett, E. J. (1995). *Aspergillus* species. Mandell, Douglas and Bennett's Principles and Practice of Infectious Diseases. J. E. B. G.L. Mandell, and R. Dolin. Churchill Livingstone, New York, pp. 2306-2310.
Bodey, G. P. et al. (1989) "Aspergillosis." Eur Journal Clinical Microbiol Infectious Diseases, vol. 8, No. 5, pp. 413-437.

(Continued)

*Primary Examiner* — Oluwatosin A Ogunbiyi
(74) *Attorney, Agent, or Firm* — Westman, Champlin & Koehler, P.A.; Z. Peter Sawicki; Visala Goswitz

(57) ABSTRACT

A method for stimulating the immune system in immunocompromised patients in order to treat opportunistic infection. The method involves the infusion of intentionally mismatched allogeneic cells. In order to prevent graft vs. host disease complications, the allogeneic cells can be irradiated prior to infusion.

9 Claims, No Drawings

(56) References Cited

OTHER PUBLICATIONS

Bozza, S. et al. (2002). "Dendritic cells transport conidia and hyphae of Aspergillus fumigatus from the airways to the draining lymph nodes and initiate disparate Th responses to the fungus." Journal of Immunology, vol. 168, No. 3, pp. 1362-1371.

Caillot, D. (2003). "Intravenous itraconazole followed by oral itraconazole for the treatment of amphotericin-B-refractory invasive pulmonary aspergillosis." Acta Haematol, vol. 109, No. 3, pp. 111-118.

Carayol, G. et al. (1997). "Quantitative analysis of T helper 1, T helper 2, and inflammatory cytokine expression in patients after allogeneic bone marrow transplantation: relationship with the occurrence of acute graft-versus-host disease." Transplantation, vol. 63, No. 9, pp. 1307-1313.

Cella, M. et al. (1996). "Ligation of CD40 on dendritic cells triggers production of high levels of interleukin-12 and enhances T cell stimulatory capacity: T-T help via APC activation." Journal Exp Med, vol. 184, No. 2, pp. 747-752.

Cenci, E. et al. (1998). "Cytokine- and T helper-dependent lung mucosal immunity in mice with invasive pulmonary aspergillosis." The Journal of Infectious Diseases, vol. 178, No. 6, pp. 1750-1760.

Cenci, E. et al. (1997). "Th1 and Th2 cytokines in mice with invasive aspergillosis." Infection and Immunity, vol. 65, No. 2, pp. 564-570.

Centeno-Lima, S. et al. (2002). "Kinetics of cytokine expression in mice with invasive aspergillosis: lethal infection and protection." FEMS Immunology and Medical Microbiology, vol. 32, No. 2, pp. 167-173.

Chen, H. D. et al. (2003). "Specific history of heterologous virus infections determines anti-viral immunity and immunopathology in the lung." American Journal of Pathology, vol. 163, No. 4, pp. 1341-1355.

Ciubotariu, R. et al. (2002). "Dendritic cells crossprime allo-specific self-restricted CD4(+) T cells after coculture with dead allogeneic cells." Human Immunology, vol. 63, No. 7, pp. 517-523.

Clemons, K. V. et al. (2000). "Role of IL-10 in invasive aspergillosis: increased resistance of IL-10 gene knockout mice to lethal systemic aspergillosis." Clinical Exp Immunology, vol. 122, No. 2, pp. 186-191.

Clerici, M. et al. (1993). "A TH1—>TH2 switch is a critical step in the etiology of HIV infection." Immunology Today, vol. 14, No. 3, pp. 107-111.

Das, H. et al. (2001). "Kinetic analysis of cytokine gene expression in patients with GVHD after donor lymphocyte infusion." Bone Marrow Transplant, vol. 27, No. 4, pp. 373-380.

de Vries, J. E. (1995). "Immunosuppressive and anti-inflammatory properties of interleukin 10." Ann Med, vol. 27, No. 5, pp. 537-541.

Deng, Y. et al. (2004). "Age-related impaired type 1 T cell responses to influenza: reduced activation ex vivo, decreased expansion in CTL culture in vitro, and blunted response to influenza vaccination in vivo in the elderly." The Journal of Immunology, vol. 172, No. 6, pp. 3437-3446.

Denning, D. W. (1996). "Therapeutic outcome in invasive aspergillosis." Clinical Infectious Diseases, vol. 23, No. 3, pp. 608-615.

Denning, D. W. (1998). "Invasive aspergillosis." Clinical Infectious Diseases, vol. 26, No. 4, pp. 781-803; quiz 804-805.

Denning, D. W. et al. (1990). "Antifungal and surgical treatment of invasive aspergillosis: review of 2,121 published cases." Reviews of Infectious Diseases, vol. 12, No. 6, pp. 1147-1201.

Dixon, D. M. et al. (1989). "Fungus dose-dependent primary pulmonary aspergillosis in immunosuppressed mice." Infection and Immunity, vol. 57, No. 5, pp. 1452-1456.

DuPont, B. et al. (1976). "Human mixed-lymphocyte culture reaction: genetics, specificity, and biological implications." Adv Immunology, vol. 23, pp. 107-202.

Elenkov, I. J. (2004). "Glucocorticoids and the Th1/Th2 balance." Annals New York Academy of Sciences, vol. 1024, pp. 138-146.

Fan, X. G., W. E. Liu, et al. (1998). "Circulating Th1 and Th2 cytokines in patients with hepatitis C virus infection." Mediators Inflamm, vol. 7, No. 4, pp. 295-297.

Fiorentino, D. F. et al. (1989). "Two types of mouse T helper cell. IV. Th2 clones secrete a factor that inhibits cytokine production by Th1 clones." The Journal of Exp Med, vol. 170, No. 6, pp. 2081-2095.

Fowler, D. H. et al. (1994). "Donor lymphoid cells of Th2 cytokine phenotype reduce lethal graft versus host disease and facilitate fully allogeneic cell transfers in sublethally irradiated mice." Prog Clin Biol Res, vol. 389, pp. 533-540.

Gazzinelli, R. T. et al. (1992). "CD4+ subset regulation in viral infection. Preferential activation of Th2 cells during progression of retrovirus-induced immunodeficiency in mice." Journal of Immunology, vol. 148, No. 1, pp. 182-188.

Grazziutti, M. et al. (2001). "Dendritic cell-mediated stimulation of the in vitro lymphocyte response to Aspergillus." Bone Marrow Transplantation, vol. 27, No. 6, pp. 647-652.

Groux, H. et al. (1996). "Interleukin-10 induces a long-term antigen-specific anergic state in human CD4+ T cells." Journal of Exp Med, vol. 184, No. 1, pp. 19-29.

Guo, H. et al. (2004). "Th1/Th2 cytokine profiles and their relationship to clinical features in patients following nonmyeloablative allogeneic stem cell transplantation." American Journal of Hematology, vol. 75, No. 2, pp. 78-83.

Hebart, H. et al. (2002). "Analysis of T-cell responses to Aspergillus fumigatus antigens in healthy individuals and patients with hematologic malignancies." Blood, vol. 100, No. 13, pp. 4521-4528.

Herbrecht, R. et al. (2002). "Voriconazole versus amphotericin B for primary therapy of invasive aspergillosis." The New England Journal of Medicine, vol. 347, No. 6, pp. 408-415.

Heufler, C. et al. (1996). "Interleukin-12 is produced by dendritic cells and mediates T helper 1 development as well as interferon-gamma production by T helper 1 cells." Eur J Immunol, vol. 26, No. 3, pp. 659-668.

Ho, P. L. et al. (2000). "Aspergillosis in bone marrow transplant recipients." Critical Reviews in Oncology/Hematology, vol. 34, No. 1, pp. 55-69.

Huffnagle, G. B. et al. (2003). "Innate and adaptive determinants of host susceptibility to medically important fungi." Current Opinion in Microbiology, vol. 6, No. 4, pp. 344-350.

Ildstad, S. T. et al. (1985). "Characterization of mixed allogeneic chimeras. Immunocompetence, in vitro reactivity, and genetic specificity of tolerance." J Exp Med, vol. 162, No. 1, pp. 231-244.

Jung, U. et al. (2003). "CD3/CD28-costimulated T1 and T2 subsets: differential in vivo allosensitization generates distinct GVT and GVHD effects." Blood, vol. 102, No. 9, pp. 3439-3446.

Kelsall, B. L. et al. (1996). "Interleukin-12 production by dendritic cells. The role of CD40-CD40L interactions in Th1 T-cell responses." Annals New York Academy of Sciences, vol. 795, pp. 116-126.

Kim, W. U. et al. (2000). "Divergent effect of cyclosporine on Th1/Th2 type cytokines in patients with severe, refractory rheumatoid arthritis." The Journal of Rheumatology, vol. 27, No. 2, pp. 324-331.

Krenger, W. et al. (1996). "Graft-versus-host disease and the Th1/Th2 paradigm." Immunol Res, vol. 15, No. 1, pp. 50-73.

Kullberg, M. C. et al. (1992). "Infection with Schistosoma mansoni alters Th1/Th2 cytokine responses to a non-parasite antigen." The Journal of Immunology, vol. 148, No. 10, pp. 3264-3270.

Kurup, V. P. et al. (1994). "Particulate Aspergillus fumigatus antigens elicit a TH2 response in BALB/c mice." J Allergy Clin Immunol, vol. 93, No. 6, pp. 1013-1020.

Kwon-Chung, K. a. J. B. (1992). Aspergillosis in Medical Mycology. Philadelphia, Lea & Febiger, pp. 201-247.

Lobashevsky, A. L. et al. (1998). "DR Non-B1 Mismatches Influence Allogeneic MLR-Induced TH1- or TH2-Like Cytokine Responses in Rhesus Monkeys." Human Immunology, vol. 59, No. 6, pp. 363-372.

Matt, P. et al. (2003). "Short- and long-term outcome after lung resection for invasive pulmonary aspergillosis." Thorac Cardiovasc Surg, vol. 51, No. 4, pp. 221-225.

(56) References Cited

OTHER PUBLICATIONS

Mailliard, R. B. et al. (2003). "Dendritic cells mediate NK cell help for Th1 and CTL responses: two-signal requirement for the induction of NK cell helper function." The Journal of Immunology, vol. 171, No. 5, pp. 2366-2373.
Meyers, J. D. (1990). "Fungal infections in bone marrow transplant patients." Seminars in Oncology, vol. 17, No. 3 Suppl. 6, pp. 10-13.
Micallef, M. J. et al. (1997). "Interleukin 18 induces the sequential activation of natural killer cells and cytotoxic T lymphocytes to protect syngeneic mice from transplantation with Meth A sarcoma." Cancer Research, vol. 57, No. 20, pp. 4557-4563.
Moore, K. W. et al. (2001). "Interleukin-10 and the interleukin-10 receptor." Annu Rev Immunol, vol. 19, pp. 683-765.
Moore, K. W. et al. (1993). "Interleukin-10." Annu Rev Immunol, vol. 11, pp. 165-190.
Morrison, B. E. et al. (2003). "Chemokine-mediated recruitment of NK cells is a critical host defense mechanism in invasive aspergillosis." The Journal of Clinical Investigation, vol. 112, No. 12, pp. 1862-1870.
Morrison, V. A. et al. (1993). "The spectrum of non-Candida fungal infections following bone marrow transplantation." Medicine (Baltimore), vol. 72, No. 2, pp. 78-89.
Mosmann, T. R. et al. (1989). "Heterogeneity of cytokine secretion patterns and functions of helper T cells." Advances in Immunology, vol. 46, pp. 111-147.
Nagai, H. et al. (1995). "Interferon-gamma and tumor necrosis factor-alpha protect mice from invasive aspergillosis." The Journal of Infectious Diseases, vol. 172, No. 6, pp. 1554-1560.
Ochs, L. A. et al. (1996). "Cytokine expression in human cutaneous chronic graft-versus-host disease." Bone Marrow Transplant, vol. 17, No. 6, pp. 1085-1092.
Okamura, H. et al. (1998). "Regulation of interferon-gamma production by IL-12 and IL-18." Current Opinion in Immunology, vol. 10, No. 3, pp. 259-264.
Patterson, T. F. (2002). "New agents for treatment of invasive aspergillosis." Clinical Infectious Diseases, vol. 35, No. 4, pp. 367-369.
Peterson, P. K. et al. (1983). "A prospective study of infectious diseases following bone marrow transplantation: emergence of Aspergillus and Cytomegalovirus as the major causes of mortality." Infection Control, vol. 4, No. 2, pp. 81-89.
Pollard, A. M. et al. (1990). "Characterization of murine lung dendritic cells: similarities to Langerhans cells and thymic dendritic cells." J Exp Med, vol. 172, No. 1, pp. 159-167.
Roilides, E. et al. (1998). "Pulmonary host defences against Aspergillus fumigatus." Res Immunol, vol. 149, Nos. 4-5, pp. 454-465; discussion 523-524.
Romagnani, S. (1991). "Human TH1 and TH2 subsets: doubt no more." Immunology Today, vol. 12, No. 8, pp. 256-257.
Ruedi, E. et al. (1989). "Antiviral T cell competence and restriction specificity of mixed allogeneic (P1+P2—P1) irradiation chimeras." Cellular Immunology, vol. 121, No. 1, pp. 185-195.
Rus, V. et al. (1995). "Kinetics of Th1 and Th2 cytokine production during the early course of acute and chronic murine graft-versus-host disease. Regulatory role of donor CD8+ T cells." The Journal of Immunology, vol. 155, No. 5, pp. 2396-2406.
Sallusto, F. et al. (1998). "Chemokines and chemokine receptors in T-cell priming and Th1/Th2-mediated responses." Immunology Today, vol. 19, No. 12, pp. 568-574.
Saxton, M. L. et al. (1997). "Adoptive transfer of anti-CD3-activated CD4+ T cells plus cyclophosphamide and liposome-encapsulated interleukin-2 cure murine MC-38 and 3LL tumors and establish tumor-specific immunity." Blood, vol. 89, No. 7, pp. 2529-2536.
Schaffner, A. et al. (1982). "Selective protection against conidia by mononuclear and against mycelia by polymorphonuclear phagocytes in resistance to Aspergillus. Observations on these two lines of defense in vivo and in vitro with human and mouse phagocytes." J Clin Invest, vol. 69, No. 3, pp. 617-631.
Selin, L. K. et al. (1998). "Protective heterologous antiviral immunity and enhanced immunopathogenesis mediated by memory T cell populations." J Exp Med, vol. 188, No. 9, pp. 1705-1715.
Sher, A., et al. (1992). "Role of T-cell derived cytokines in the downregulation of immune responses in parasitic and retroviral infection." Immunology Reviews, No. 127, pp. 183-204.
Shinomiya, Y. et al. (1995). "Anti-metastatic activity induced by the in vivo activation of purified protein derivative (PPD)-recognizing Th1 type CD4+ T cells." Immunobiology, vol. 193, No. 5, pp. 439-455.
Shurin, M. R. et al. (1999). "Th1/Th2 balance in cancer, transplantation and pregnancy." Springer Semin Immunopathol 21(3): 339-359.
Steinbrink, K. et al. (1997). "Induction of tolerance by IL-10-treated dendritic cells." The Journal of Immunology, vol. 159, No. 10, pp. 4772-4780.
Stevens, D. A. et al. (2000). "Practice guidelines for diseases caused by Aspergillus. Infectious Diseases Society of America." Clinical Infectious Diseases, vol. 30, No. 4, pp. 696-709.
Stumbles, P. A. et al. (1998). "Resting respiratory tract dendritic cells preferentially stimulate T helper cell type 2 (Th2) responses and require obligatory cytokine signals for induction of Th1 immunity." J Exp Med, vol. 188, No. 11, pp. 2019-2031.
Toungouz, M. et al. (1995). "HLA DR subtypes induce IL-6 and TNF-alpha production in the primary mixed lymphocyte reaction." Transplantation Proceedings, vol. 27, No. 1, pp. 461-462.
Trinchieri, G. (1989). "Biology of natural killer cells." Advances in Immunology, vol. 47, pp. 187-376.
Trinchieri, G. (1995). "Natural killer cells wear different hats: effector cells of innate resistance and regulatory cells of adaptive immunity and of hematopoiesis." Seminars in Immunology, vol. 7, No. 2, pp. 83-88.
Wald, A. et al. (1997). "Epidemiology of Aspergillus infections in a large cohort of patients undergoing bone marrow transplantation." The Journal of Infectious Diseases, vol. 175, No. 6, pp. 1459-1466.
Walsh, T. J. et al. (1999). "Liposomal amphotericin B for empirical therapy in patients with persistent fever and neutropenia. National Institute of Allergy and Infectious Diseases Mycoses Study Group." The New England Journal of Medicine, vol. 340, No. 10, pp. 764-771.
Whary, M. T. et al. (2004). "Th1-mediated pathology in mouse models of human disease is ameliorated by concurrent Th2 responses to parasite antigens." Current Topics in Medicinal Chemistry, vol. 4, No. 5, pp. 531-538.
Williams, M. A. et al. (2003). "Primary and secondary immunocompetence in mixed allogeneic chimeras." The Journal of Immunology, vol. 170, No. 5, pp. 2382-2389.
Wingard, J. R. et al. (1999). "Clinical significance of nephrotoxicity in patients treated with amphotericin B for suspected or proven aspergillosis." Clinical Infectious Diseases, vol. 29, No. 6, pp. 1402-1407.
Yamamura, M. (1992). "Defining protective responses to pathogens: cytokine profiles in leprosy lesions." Science, vol. 255, No. 5040, p. 12.
Substantive Examination Report, Israeli Patent Application No. 194667. "Pharmaceutical Compositions Containing Allogeneic Cells." Jul. 5, 2012.
Ottinger et al. Blood, 2003, 102:1131-1137.
Kanda et al. (Blood 2003 102:1131-1137.
Stem Cell Basics: What are the similarities and differences between embryonic and adult stem cells? In Stem Cell Information [World Wide Web site]. Bethesda, MD: National Institutes of Health, U.S. Department of Health and Human Services, 2011 [cited Wednesday Jun. 15, 2011] Available at <http://stemcells.nih.gov/info/basics/basics5>.
Stem Cell Basics: What are adult stem cells? In Stem Cell Information [World Wide Web site]. Bethesda, MD: National Institutes of Health, U.S. Department of Health and Human Services, 2010 [cited Wednesday Jun. 15, 2011] Available at <http://stemcells.nih.gov/info/basics/basics4>.
The Adult Stem Cell. In Stem Cell Information [World Wide Web site]. Bethesda, MD: National Institutes of Health, U.S. Department

(56) References Cited

OTHER PUBLICATIONS of Health and Human Services, 2009 [cited Wednesday Jun. 15, 2011] Available at <http://stemcells.nih.gov/info/scireport/chapter4>.
Verda et al. Stem Cells 2008; 26: 381-386.

* cited by examiner

ALLOGENEIC CELLULAR IMMUNOTHERAPY FOR OPPORTUNISTIC INFECTION

CROSS-REFERENCE TO RELATED APPLICATION

The present application is a continuation of and claims priority of U.S. patent application Ser. No. 11/251,585, filed Oct. 14, 2005, now U.S. Pat. No. 8,865,224, which is based on and claims the benefit of U.S. provisional patent application Ser. No. 60/618,682, filed Oct. 14, 2004, the contents of which are hereby incorporated by reference in their entirety.

FIELD OF THE INVENTION

This invention relates to the use of allogeneic cell infusions to treat disease. More particularly, the invention relates to an allogeneic cell therapy for the stimulation of cellular immunity in immunocompromised hosts.

BACKGROUND

The human immune system is capable of protecting individuals from infection by a variety of bacterial, protozoal, fungal, and viral pathogens. However, when the immune system is weakened by age or disease (e.g., HIV infection) or by medication (corticosteroids, chemotherapy) or by treatments to prevent rejection in organ or bone marrow transplantation patients, these pathogens that normally do not cause clinic disease can cause infections. The common opportunistic pathogens are fungi, *Mycobacterium avium* cellulare, viruses, particularly cytomegalovirus infection (CMV), and *Pneumocystis carinii*. Patients with HIV infection, organ and bone marrow transplants are particularly vulnerable to opportunistic infections.

The immunosuppressed individual is vulnerable to both endogenous and external organisms. Opportunistic infections can result from exogenous acquisition of a particularly virulent pathogen (eg, meningococcal meningitis or pneumococcal pneumonia), reactivation of an endogenous latent organism (eg, herpes simplex virus (HSV), herpes zoster virus (HZV or shingles), or tuberculosis, and endogenous invasion of a normally commensal or saprophytic organisms (eg, bacteria, viruses, fungi, or protozoa/parasites). The exact type of opportunistic infection that occurs depends on the type and extent of immunologic alteration, whether it be cellular, humoral, phagocytic, or a combined defect; and on organisms present in the internal and external environments.

Opportunistic infections are often lethal despite treatment with anti-viral, anti-fungal or antibiotic medications. Therefore, there is a need to develop methods to strengthen the immune system of immunocompromised individuals to both treat and prevent opportunistic infection.

SUMMARY OF THE INVENTION

The present invention comprises a method for stimulating the immune system in immunocompromised patients in order to treat opportunistic infection. The method involves the infusion of intentionally mismatched allogeneic cells. In order to prevent graft vs. host disease complications, the allogeneic cells can be irradiated prior to infusion.

DETAILED DESCRIPTION OF ILLUSTRATIVE EMBODIMENTS

*Aspergillus* is a prototypical opportunistic organism. *Aspergillus* is a filamentous, cosmopolitan and ubiquitous fungus found in nature. It is commonly isolated from soil, plant debris, and the indoor air environment. Aspergillosis is a large spectrum of diseases caused by members of the genus *Aspergillus*. Among all filamentous fungi, *Aspergillus* is in general the one most commonly isolated in invasive infections. It is the second most commonly recovered fungus in opportunistic mycoses following Candida (Kwon-Chung 1992). *Aspergillus fumigatus* is also the most common cause of invasive aspergillosis (IA).

IA is a fulminant and highly lethal infection that is common in immunocompromised patients (Bodey and Vartivarian 1989; Denning 1998). Immunosuppression is the major factor predisposing to development of opportunistic infections (Ho and Yuen 2000). Colonization of the respiratory tract is very common. The infection is initiated upon inhalation of conidia (fungal spores) by immunocompromised patients. Conidia are efficiently cleared from the lungs in healthy individuals, but in immunocompromised patients they can germinate to form hyphae that invade the surrounding tissues, resulting in a severe and progressive pneumonia that can subsequently disseminate to other organs. The clinical manifestation and severity of the disease depends upon the immunologic state of the patient (Bennett 1995). Lowered host resistance due to such factors as underlying debilitating disease, neutropenia chemotherapy, disruption of normal flora, or an inflammatory response due to the use of antimicrobial agents and steroids can predispose patients to colonization, invasive disease, or both (Morrison, Haake et al. 1993).

Therapy for IA is associated with poor outcomes with an overall mortality rate of approximately 60% (Stevens, Kan et al. 2000). IA is an especially serious problem following bone marrow transplantation (BMT) due to steroid-induced immunosuppression and chemotherapy-induced neutropenia (Peterson, McGlave et al. 1983; Meyers 1990).

The antifungal agents approved for the treatment of IA have clinical response rates ranging from 33% to 52% (Patterson 2002). Current therapies for IA include: voriconazole (Herbrecht, Denning et al. 2002); amphotericin B, which causes nephrotoxicity in 80% of patients (Wingard, Kubilis et al. 1999); liposomal amphotericin B which is a less nephrotoxic formulation (Walsh, Finberg et al. 1999), but can be hepatotoxic and is highly expensive; itraconazole which has many drug interactions (Caillot 2003); surgical excision of infarcted tissue (Matt, Bernet et al. 2003); and caspofungin, recently approved by the US Food and Drug Administration as salvage therapy for IA patients refractory or intolerant to other therapies. However, despite aggressive anti-fungal therapy, the prognosis for IA in BMT patients remains extremely poor with mortality rates of 90% or more (Denning and Stevens 1990; Denning 1996).

Because treatment outcomes remain suboptimal for IA, new approaches for therapy are required. Methods that can stimulate cellular (Th1) immunity are thought to be the most effective in treating opportunistic viral and fungal infection.

Th1/Th2 Immunity

Adaptive immunity is characterized as Th1 or Th2 depending on the predominant type of CD4+ T-cell involved in the response. The balance of cytokines produced by Th1 cells and Th2 cells is a key factor influencing the character of an immune response. The functional division of CD4+ lymphocytes into Th1 and Th2 subsets is based upon their cytokine profile. Th1 cells produce gamma interferon (IFN-γ) and interleukin-2 (IL-2), but not IL-4. Th2 cells produce IL-4 and IL-10, but not IFN-γ (Mosmann and Coffman 1989; Romagnani 1991). Cytokines produced by these two subsets are mutually inhibitory and establish a reciprocal cross regulation. Th1 cells inhibit the proliferation of Th2 cells and Th2 cells inhibit Th1 cell cytokine production (Fiorentino, Bond et al. 1989). This cross regulation results in a polarized Th1 or Th2 immune response to pathogens that can determine either host resistance or susceptibility to infection. Th1 cells differentiate in the presence of IL-12 (and potentiated by IL-18) secreted by dendritic cells (DC), while Th2 cells differentiate under the influence of IL-4 produced by NKT cells, basophils, eosinophils, and mast cells. A Th1 response in protozoan, viral or fungal infection is associated with resistance, while a Th2 response to these pathogens is associated with disease (Kawakami 2003).

Natural Infection Control

Activation of both innate and adaptive immune mechanisms are essential for host control of fungal infection. Effector mechanisms of the innate immune system are a major defense against IA (Roilides, Katsifa et al. 1998). Resistance to infection requires unimpaired innate antifungal activity of pulmonary phagocytic cells operating in a cytokine environment rich in TNF-α and IL-12, as well as the presence of interstitial T-cells producing IL-2 and IFN-γ (Cenci, Mencacci et al. 1998). Resident alveolar macrophages ingest and kill resting condia, while neutrophils attack hyphae germinating from condia that escape macrophage surveillance (Schaffner, Douglas et al. 1982). The effectiveness of this immune response is evident from the observation that challenge, even with a large number of condia, fails to cause disease in immunocompetent animals (Dixon, Polak et al. 1989).

Dendritic cells (DC) are the innate immune cells recognized as initiators of the immune response to pathogens, including *Aspergillus*, and serve as a bridge between innate and adaptive immunity. DC have a primary role in surveillance for pathogens at the mucosal surfaces (Banchereau and Steinman 1998). A dense network of DC has been described in the respiratory tracts (Pollard and Lipscomb 1990). In the resting state, respiratory tract DC are specialized for uptake and processing, but not for presentation of antigen (Ag), the latter requiring cytokine maturation signals (Stumbles, Thomas et al. 1998).

Immature DC in the respiratory track recognize and phagocytose fungus. Upon phagocytosis and signaling from inflammatory cytokines, such as TNF-DC become activated and then migrate as mature DC to the lymph nodes (Bozza, Gaziano et al. 2002; Bauman, Huffnagle et al. 2003). Mature DC in turn activate naïve T-cells in the lymph nodes via presentation of fungal antigen in the context of MHC I and MHC II molecules, concurrent with the expression of co-stimulatory molecules. Cytokine production by DC determines the development of either a Th1 or Th2 adaptive immune response (Huffnagle and Deepe 2003).

In murine models of aspergillosis, Th1 cytokines correlate with protection from disease while Th2 cytokines correlate with susceptibility (Nagai, Guo et al. 1995; Cenci, Perito et al. 1997). Development of protective adaptive immunity is associated with activation of Th1 cells producing IFN-γ and macrophages producing IL-12. Consistent with this observation, neutralization of the Th2 cytokine, IL-4, or administration of the Th1 cytokine, IFN-γ has a curative effect on *Aspergillus* infection, whereas IFN-γ neutralization and increased production of the Th2 cytokine, IL-10, results in increased pathology (Nagai, Guo et al. 1995). Th1 immune responses have also been shown to successfully control IA in patients with hematological malignancies (Hebart, Bollinger et al. 2002)

Post Engraftment Immunity

Patients with an impaired cellular immune response are predisposed to cancer and infection. Impaired cellular immunity can be triggered by the presence of malignant or viral diseases, or iatrogenically through immunosuppressive drugs, transplantation, chemotherapy, or irradiation. Impaired cellular immunity and disease is correlated with imbalances in Th1/Th2 cytokines in favor of Th2 immunity and effector function (Shurin, Lu et al. 1999; Kidd 2003). Enhanced Th2 responses, creating an immunosuppressed state, are present in infectious diseases such as chronic hepatitis C virus infection (Fan, Liu et al. 1998), leprosy (Yamamura 1992), helminth, protozoa and retrovirus infection (Gazzinelli, Makino et al. 1992; Sher, Gazzinelli et al. 1992), AIDS (Clerici and Shearer 1993) and as part of the aging process (Deng, Jing et al. 2004).

In the allogeneic BMT setting, allogeneic cell infusions elicit an anti-tumor effect called the graft vs. tumor (GVT) effect mediated through the enhancement of Th1 immunity (Jung; Foley et al. 2003). The enhanced Th1 immunity after allogeneic BMT is also correlated with effective immune surveillance for prevention or delay in cancer relapse (Guo, Qiao et al. 2004). However, the beneficial effects of GVT are often offset by the occurrence of graft-vs-host disease (GVHD), which remains the major complication of allogeneic BMT.

GVHD is initiated by alloreactive donor T-cells recognizing foreign HLA (Human Leukocyte Antigen) antigens of the host. Dysregulation of cytokine networks is the primary cause of GVHD (Krenger and Ferrara 1996). Th1 cytokine release dominates in GVHD (Rus, Svetic et al. 1995; Ochs, Blazar et al. 1996; Das, Imoto et al. 2001), while Th2 cells inhibit GVHD lethality (Fowler, Kurasawa et al. 1994). Therapy for chronic GVHD is highly immunosuppressive and must be continued for a prolonged time. The most widely employed first line therapy for treatment of chronic GVHD is a cyclosporine A (CSA) and prednisone regimen. Both CSA (Kim, Cho et al. 2000) and prednisone (Elenkov 2004) treatment tends to inhibit Th1 immunity and promote Th2 immunity.

GVHD control requires suppression of cellular immune mechanisms and enhancement of Th2 immunity Immunosuppression to control GVHD makes patients susceptible to opportunistic infection from a broad array of pathogens. These infections, including *aspergillus* infection, are the major cause of death secondary to GVHD, followed by progressive organ failure from the chronic GVHD immune response. Immunosuppressed patients have high levels of IL-10 in plasma. IL-10 is produced by Th2 lymphocytes, macrophages, mast cells and B-cells (Moore, O'Garra et al. 1993) and has potent immunosuppressive properties, capable of enhancing Th2 immune responses and inhibiting differentiation of a Th1 response (de Vries 1995). Treatment of GVHD with glucocorticoids directly enhances the induction of IL-10-producing T cells. IL-10 is known to inhibit the production of IL-12 and the expression of MHC class II Ags and costimulatory molecules by macrophages, monocytes, and various types of dendritic cells (Moore, de Waal Malefyt et al. 2001). Furthermore, IL-10 treatment of dendritic cells contributes to a state of anergy in alloantigen-activated T cells (Groux, Bigler et al. 1996; Steinbrink, Wolfl et al. 1997). *Aspergillus* is also capable of directly stimulating the production of IL-10 (Clemons, Grunig et al. 2000). Particulate *Aspergillus* antigens have been shown to elicit Th2 responses in Balb/c mice (Kurup, Seymour et al. 1994).

Therefore, the challenge of designing an immunotherapy to treat IA and other opportunistic infections in the post-engraftment BMT setting is to design a method to enhance anti-pathogen Th1 immunity in an immunosuppressed, Th2-biased setting without exacerbating GVHD.

Allogeneic Cell Therapy

In order to develop an effective immunotherapy for IA and other opportunistic infections in the post-engraftment BMT setting, it is necessary to first stimulate innate immunity and then induce a fungus-specific (or other pathogen-specific) Th1 adaptive immune response against a background of immunosuppressive drugs, as well as existing and imprinted Th2 skewed immunity to the offending pathogen. An additional challenge is the need to elicit Th1 anti-fungal (or other pathogen-specific) immunity in this background without concurrent stimulation of Th1-mediated GVHD.

In general, generation of an effective Th1 adaptive immune response requires a defined cascade of immunological events that must occur under rigorously controlled conditions. The infusion of HLA-mismatched allogeneic cells into an immunocompromised host elicits a strong host allorecognition response capable of triggering this cascade of events. These events include: (i) the activation of innate effector mechanisms causing the shedding of fungal (or other) antigen (Ag); (ii) the uptake and processing of fungal (or other) Ag by dendritic cells in the lungs; (iii) the migration of the dendritic cells to the draining lymph nodes and the subsequent presentation of fungal (or other) Ag in the context of MHC I or MHC II molecules to naïve T-cells; (iv) the conditioning of the lymph node microenvironment for differentiation of Th1 effector cells; (v) the migration and extravasation of primed fungal-specific (or other) Th1 effector cells to the site of infection; and (vi) effector cell recognition and clearing of fungus (or other pathogen) from the tissue. All these events must occur in the context of a sustained pro-inflammatory Th1 cytokine environment. Failure of any of these events to occur in the correct cytokine context will result in an inadequate anti-fungal (or other) immune response.

Therefore, in order to create an environment conducive to development of de-novo Th1 antifungal (or other) immunity, it is first necessary to induce the expression of Th1 cytokines and maintain this cytokine environment during the activation of innate immune effector cells and until the establishment of an anti-fungal (or other) Th1 adaptive immune response. The presence of Th1 cytokines will down regulate the existing Th2 cytokines. In order to initially change the existing Th2-dominated immune environment in the fungal-infected immunocompromised host, infuse HLA-mismatched allogeneic lymphocytes, preferably activated Th1 lymphocytes expressing high density CD40L. Infusion of HLA-mismatched allogeneic cells elicits a burst of Th1 cytokines from host immune cells as part of the rejection response. It is known that a predominance of Th1 cytokines are produced after allogeneic cell infusion (Carayol, Bourhis et al. 1997). Further, it has been observed that in mixed lymphocyte reactions, allogeneic stimulator cells elicit production of Th1 cytokines from responder cells (DuPont and Hansen 1976; Toungouz, Denys et al. 1995). In addition, T cell stimulation by multiple HLA mismatches in rhesus macaques facilitates polarization toward a proinflammatory Th1-like response in vitro and in vivo in transplant recipients (Lobashevsky, Wang et al. 1998). There is also a predominance of Th1 type cytokines in the development of human GVHD induced by allogeneic cell infusion (Das, Imoto et al. 2001).

Clinically, reduced numbers or impaired function of neutrophils are by far the best-characterized risk factors for invasive aspergillosis (Wald, Leisenring et al. 1997). Th1 cytokine production as a result of the allogeneic cell infusion will serve to activate alternative anti-fungal innate effector cells. The Th1 cytokines (predominantly IFN-γ, TNF-α, IL-1, IL-2, IL-12 and IL-18) produced as a result of the allogeneic cell infusion and the rejection response activate alternative innate immune effector cells such as NK cells and DC, as well activate T-cells (Antin and Ferrara 1992). In turn, these cells produce Th1 cytokines which create an autocrine and paracrine cytokine network serving to both maintain and enhance the production of Th1 cytokines (Mailliard, Son et al. 2003). Activated innate immune cells produce IL-12 and IL-18, which synergistically act in autocrine feedback loop to enhance the production of IFN-γ (Micallef, Tanimoto et al. 1997; Okamura, Kashiwamura et al. 1998). The production of IFN-γ by activated NK cells functions in the priming process of Th1 cells, which in turn supports the expansion and effector function of CD8+ CTLs in the Th1 adaptive immune response (Trinchieri 1995).

The activation of NK cells and DC by the Th1 cytokines produced in response to the allogeneic infusion are essential elements for generating de-novo fungal Ag shedding and presentation to T-cells in a Th1-steering environment. NK cells are essential for protection against viruses, parasites, bacteria as well as fungi (Trinchieri 1989). In immunocompromised hosts, recruitment of NK cells to the lungs has been shown to be an effective defense mechanism against IA (Morrison, Park et al. 2003). DCs orchestrate the overall antifungal immune resistance in the lungs and were also found to be essential in the activation of Th1 responses to *aspergillus*, in vivo (Bozza, Gaziano et al. 2002) and in vitro (Grazziutti, Przepiorka et al. 2001).

DCs become activated in the presence of Th1 cytokines. Activated DC should subsequently traffic to draining lymph nodes after uptake of fungal Ag. These DC will have enhanced ability for presentation of antigenic products of these pathogens to T-cells via the MHC I and MHC II pathways. Activated DC are capable of producing IL-12 following exposure to fungal Ag and IL-12 production by DC has been shown to induce Th1 immunity (Heufler, Koch et al. 1996). It is further hypothesized that the host T-cells activated by Th1 cytokines resulting from the allogeneic rejection response will express the CD40L surface marker. CD40L is expressed on the surface of activated T-cells. CD40 ligation of DC by CD40L-expressing T-cells triggers enhanced DC IL-12 production and enhances upregulation of co-stimulatory molecules and the capacity to present Ag (Cella, Scheidegger et al. 1996; Kelsall, Stuber et al. 1996). CD40-CD40L interaction is crucial for the IL-12-dependent priming of Th1 cells in vivo (Kelsall, Stuber et al. 1996).

The foreign MHC antigens expressed by the infused allogeneic cells are either taken up by host APC in a conventional self-MHC restricted manner (indirect alloreactivity) and/or are recognized directly on the surface of the infused cells by the T-cell receptor (TCR) of the host T-cells (direct alloreactivity). The host allogeneic response by either mechanism will result in the rejection of the infused cells and the establishment of Th1 adaptive immunity specific to the alloantigens (Ciubotariu, Tsang et al. 2002). It is hypothesized that in the presence of adjuvant Th1 cytokines, a pool of Th1 memory cells specific for the alloantigens will develop in the host. Subsequent allogeneic cell infusions should activate these resulting allo-specific memory cells. Activated memory cells express chemokine receptors CCR5, CCR2 or CCR3 that stimulate the upregulation of adhesion receptors in the lung endothelium and permit extravasation to sites of local fungal infection (Sallusto, Lanzavecchia et al. 1998). The non-specific infiltration and cytokine production of activated Th1 memory cells at the site of fungal infection has a potent stimulatory effect on local innate and adaptive immune cells responding to the fungus.

When the immune system is biased by a high frequency of memory cells specific for a given pathogenic antigen, the activation of these cells during an unrelated pathogen infection can significantly enhance clearance of the unrelated infection (Selin, Varga et al. 1998). The pathogenesis of viral infections in the lung has been shown to be related to the host experience with unrelated pathogens (Chen, Fraire et al. 2003). This immunological mechanism is known as "heterologous immunity" (Selin, Varga et al. 1998; Chen, Fraire et al. 2003). Therefore, multiple allogeneic cell infusions can create a memory pool that will enhance anti-fungal (or other opportunistic organism) immunity by the same or similar mechanism.

Background support for this described mechanism of immunity to opportunistic organisms by enhanced Th1 immunity to an alloantigen causing a switch in existing Th2 immunity to a resident infection to Th1 immunity is supported by several observations. For example, the opposite shift occurs in infection with Schistosoma mansoni which induces a Th2 immune response. This response causes a down-regulation of existing Th1 responses and elevation of Th2 responses to unrelated foreign immunogens (Kullberg, Pearce et al. 1992). Th1-mediated pathology in mouse models of disease can be ameliorated by concurrent infection with an unrelated parasite which elicits Th2 immunity (Whary and Fox 2004). Adoptive immunotherapy can induce anti-tumor activity through the production of Th1 cytokines, even though the transferred cells are not able to recognize tumor antigens. For example, polyclonal Th1 cells administered to mice with non-immunogenic tumors resulted in rejection of 60-90% of the tumors. Cured animals developed a tumor-specific memory and were capable of rejecting rechallenges with the same tumor (Saxton, Longo et al. 1997). Similarly, co-injection of a PPD-specific Th1 clone and PPD antigen in a murine metastatic tumor model produced anti-metastatic effects and anti-tumor activity (Shinomiya, Harada et al. 1995).

That Th1 immunity to fungus can be induced in an immunosuppressed host is supported by the observation that immunization of cortisone immunosuppressed mice with multiple injections of *A. fumigatus* confers protection to rechallenge with a lethal dose of condia in the context of increased production of Th1 cytokines (Centeno-Lima, Silveira et al. 2002). In addition, Th1 immunity can be preserved (Williams, Adams et al. 2003) and also be induced in chimeric hosts (Ildstad, Wren et al. 1985; Ruedi, Sykes et al. 1989).

In conclusion, multiple infusions of HLA-mismatched allogeneic cells, preferably activated Th1 cells expressing high density CD40L, into immunocompromised hosts with opportunistic infection causes a burst of Th1 cytokines that will serve as the background in which activated cells of both the innate and adaptive immune system will generate a de-novo Th1 immune response against the pathogen.

The allogeneic cell infusions are preferably activated Th1 cells from a HLA-mismatched donor. The allogeneic cells should be irradiated prior to infusion into immunocompromised patients to prevent engraftment and GVHD.

A preferred protocol is to first prime the patient with an intravenous infusion of allogeneic cells of dosages between $1\times10^6$ to $1\times10^{10}$ cells. After at least 7 days, inject additional allogeneic cells mixed with a source of antigens from the pathogen (preferably freeze/thawed organisms) and inject the mixture intradermally. If necessary, additional intradermal or intravenous injections of either the alloantigen source alone or mixed with the pathogen antigen source can be administered as booster injections.

EXAMPLES

The Animal Model

*A. fumigatus* was subcultured in potato-dextrose agar slants for 5 days at 27° C. Conidia were harvested from cultures with 0.1% phosphate-buffered saline (PBS) Tween 20. Conidia suspension was centrifuged for 2 min at 13 000×g, supernatant rejected, and cells counted. The concentration was adjusted to administer $10^7$ or $10^8$ conidia per mouse in a volume of 20 µl of sterile PBS Tween 20. Mice were immunosuppressed by intraperitoneal administration of four doses of 250 mg/kg of cortisone acetate as follows: (a) 3 days before infection, (b) on infection day, and (c) at day 2 and day 4 after infection. Cortisone-treated mice infected with a high inoculum of *A. fumigatus* conidia developed a lethal infection, while immunocompetent mice infected with the same inoculum were able to control the fungus.

Allogeneic Th1 Cells

Th1 cells were prepared from Balb/c mice. Spleen cells from the mice were harvested and ACK lysed. T1 cells were generated using anti-CD3 and anti-CD28 (CD3/CD28)-coated magnetic beads at a bead/T cell ratio of 3:1 with 20 IU/mL recombinant human IL-2, 20 ng/mL rhIL-7, 10 ng/mL recombinant murine IL-12, 10 µg/mL antimurine IL-4 mAb and 3.3 mM N-acetyl-cysteine in RPMI 1640 complete media containing 10% FBS, penicillin-streptomycin-glutamine, nonessential amino acids (NEAA), and 2-mercaptoethanol (2-ME; Life Technologies). Cytokine-containing complete media was added daily from days 2 to 6 to maintain cell concentration between 0.2 and $1.0\times10^6$ cells/mL. However, rmIL-12 was only added on day 0 of culture. After 5 days, in culture, the cells were mixed with anti-CD3/anti-CD28 coated biomagnetic particles (Miltenyi) and harvested for use on day 6.

Example #1

Immunosuppressed C57BL/6 mice were inoculated with a lethal dose ($10^7$ conidia) of fungus. The mice were divided into an untreated control group, a single allogeneic infusion group and a vaccinated group (n=8 in each group).

The single allogeneic infusion group received an iv infusion of $1\times10^6$ activated allogeneic CD4+ Th1 cells (irradiated) on day 7 post inoculum.

The vaccinated group received a priming dose of $1\times10^6$ activated allogeneic CD4+ Th1 cells (irradiated) on day 7 post inoculum. On day 14, the mice were injected intradermally in the hind leg with $1\times10^4$ activated allogeneic CD4+ Th1 cells mixed with supernatant from $10^6$ conidia that had previously undergone 2 cycles of freezing and thawing.

The infection of immunosuppressed mice resulted in 100% mortality after 5-7 days, while all the immunocompetent infected mice survived. Necropsies of death mice organs revealed fungal invasion and destruction of the organs observed (brain, lungs and kidneys).

The mice with a single infusion survived a mean of 22 days post-infection (12-28 day range).

The 5 of 8 vaccinated mice survived greater than 30 days with no evidence of infection.

These data demonstrate that allogeneic cell infusion can lead to fungus control and mice survival.

Although the present invention has been described with reference to preferred embodiments, workers skilled in the art will recognize that changes may be made in form and detail without departing from the spirit and scope of the invention.

What is claimed is:

1. A method of generating a de-novo Th1 anti-pathogen immunity in a host comprising:

inducing expression of Th1 cytokines by administering allogeneic, activated Th1-cells wherein the allogeneic cells are T-cells that have not been exposed to the pathogen, are activated through CD3/CD28 cell surface moieties, irradiated and HLA-mismatched to the host, wherein the host is immunosuppressed, has a Th2-biased immunity and is susceptible to or has developed an opportunistic infection by the pathogen due to immunosuppression;

maintaining the Th1 cytokine environment during the activation of innate immune effector cells and until establishment of an anti-pathogen Th1 adaptive immune response developed by the host immune response.

2. The method of claim 1 wherein the innate immune effector cells comprise NK cells and DC.

3. The method of claim 1 wherein the allogeneic cells are administered intravenously.

4. The method of claim 1 wherein the maintaining comprises administration of additional allogeneic cells.

5. The method of claim 4 wherein the additional allogeneic cells are administered intradermally or intravenously.

6. The method of claim 1 wherein the maintaining comprises administration of allogeneic cells and pathogen antigens.

7. The method of claim 1 wherein the pathogen is a member of the genus *Aspergillus*.

8. The method of claim 1 wherein the inducing and maintaining are performed without exacerbating GVHD in the host.

9. The method of claim 1, wherein the T-cells express high density of CD40L.

* * * * *